US00PP27781P3

(12) United States Plant Patent
Eveleens

(10) Patent No.: US PP27,781 P3
(45) Date of Patent: Mar. 14, 2017

(54) ***HYDRANGEA* PLANT NAMED 'HORTMACLEPA'**

(50) Latin Name: *Hydrangea macrophylla*
Varietal Denomination: HORTMACLEPA

(71) Applicants: Horteve Breeding BV, De Kwakel (NL); Kolster Holding BV, Boskoop (NL)

(72) Inventor: Cornelis Pieter Eveleens, Aalsmeer (NL)

(73) Assignees: Horteve Breeding B.V., Aalsmeer (NL), part interest; Kolster Holding B.V., Boskoop (NL), part interest ( * ) Notice: Subject to any disclaimer, the term of this patent is extended or adjusted under 35 U.S.C. 154(b) by 14 days.

(21) Appl. No.: 14/756,638

(22) Filed: Sep. 28, 2015

(65) Prior Publication Data

US 2016/0183431 P1 Jun. 23, 2016

(30) Foreign Application Priority Data

Dec. 19, 2014 (QZ) ..... PBR 2014/3503

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — Penny J. Aguirre

(57) ABSTRACT

A new cultivar of *Hydrangea macrophylla* plant named, 'HORTMACLEPA', that is characterized by its inflorescences with sterile florets with sepals that are white in color with thin dark pink margins (picotee) that retain their picotee color until the antique/autumn phase, and have ruffled margins.

2 Drawing Sheets

Botanical classification: *Hydrangea macrophylla.*
Varietal denomination: 'HORTMACLEPA'.

BACKGROUND OF THE INVENTION

The present invention relates to a new and distinct cultivar of *Hydrangea macrophylla* and will be referred to hereafter by its cultivar name, 'HORTMACLEPA'. 'HORTMACLEPA' represents a new mophead type *Hydrangea*, a deciduous shrub grown for use as a landscape plant and as a cut flower.

The new cultivar was derived from an ongoing controlled breeding program conducted by the Inventor in Boskoop, The Netherlands. The goal of the breeding program is to develop new cultivars of *Hydrangea* with good cut flower qualities with unique flower colors. The objective with this new cultivar was to obtain a plant with sterile floret sepals that were white with a pink edge with good substance. 'HORTMACLEPA' was derived from a cross made in May of 2009 between proprietary plants from the Inventor's breeding program reference no. 07-036-01 (not patented) as the female parent and reference no. 07-120-06 (not patented) as the male parent. 'HORTMACLEPA' was selected in June of 2012 as a single unique plant from amongst the resulting seedlings.

Asexual propagation of the new cultivar was first accomplished by stem cuttings in Boskoop, The Netherlands by the Inventor in August of 2011. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HORTMACLEPA' as a unique cultivar of *Hydrangea.*

1. 'HORTMACLEPA' exhibits sterile florets with sepals that are white in color with thin dark pink margins (picotee).
2. 'HORTMACLEPA' exhibits sterile florets with sepals that retain their picotee coloration until the antique/autumn phase.
3. 'HORTMACLEPA' exhibits sterile florets with sepals that have ruffled margins.

The female parent of 'HORTMACLEPA' differs from 'HORTMACLEPA' in having sterile florets with sepals that open white with a pink edge but quickly change to pink with a darker pink margin and lacking ruffled sepal margins. The male parent of 'HORTMACLEPA' differs in having taller stems and in having sterile florets with sepals that have a weaker substance. 'HORTMACLEPA' can be most closely compared to the *Hydrangea* cultivars 'HORTMAFLAM' (U.S. Plant patent application Ser. No. 14/756,640) and 'Spike' (U.S. Plant Pat. No. 26,826). 'HORTMAFLAM' is similar to 'HORTMACLEPA' in having picotee colored sepals that do not turn pink until the antique/autumn phase. 'HORTMAFLAM' differs from 'HORTMACLEPA' in having a larger quantity of sterile florets with a weaker substance and sepal margins that are not ruffled. 'Spike' is similar to 'HORTMACLEPA' in having sterile florets with ruffled sepal margins. 'Spike' differs from 'HORTMACLEPA' in having sterile florets with sepals that are pink in color.

BRIEF DESCRIPTION OF THE DRAWINGS

The accompanying colored photographs illustrate the overall appearance and distinct characteristics of the new

*Hydrangea*. The photographs were taken of a three year-old plant of 'HORTMACLEPA' as grown in a 3-liter container in a greenhouse in Boskoop, The Netherlands.

Figure 1:
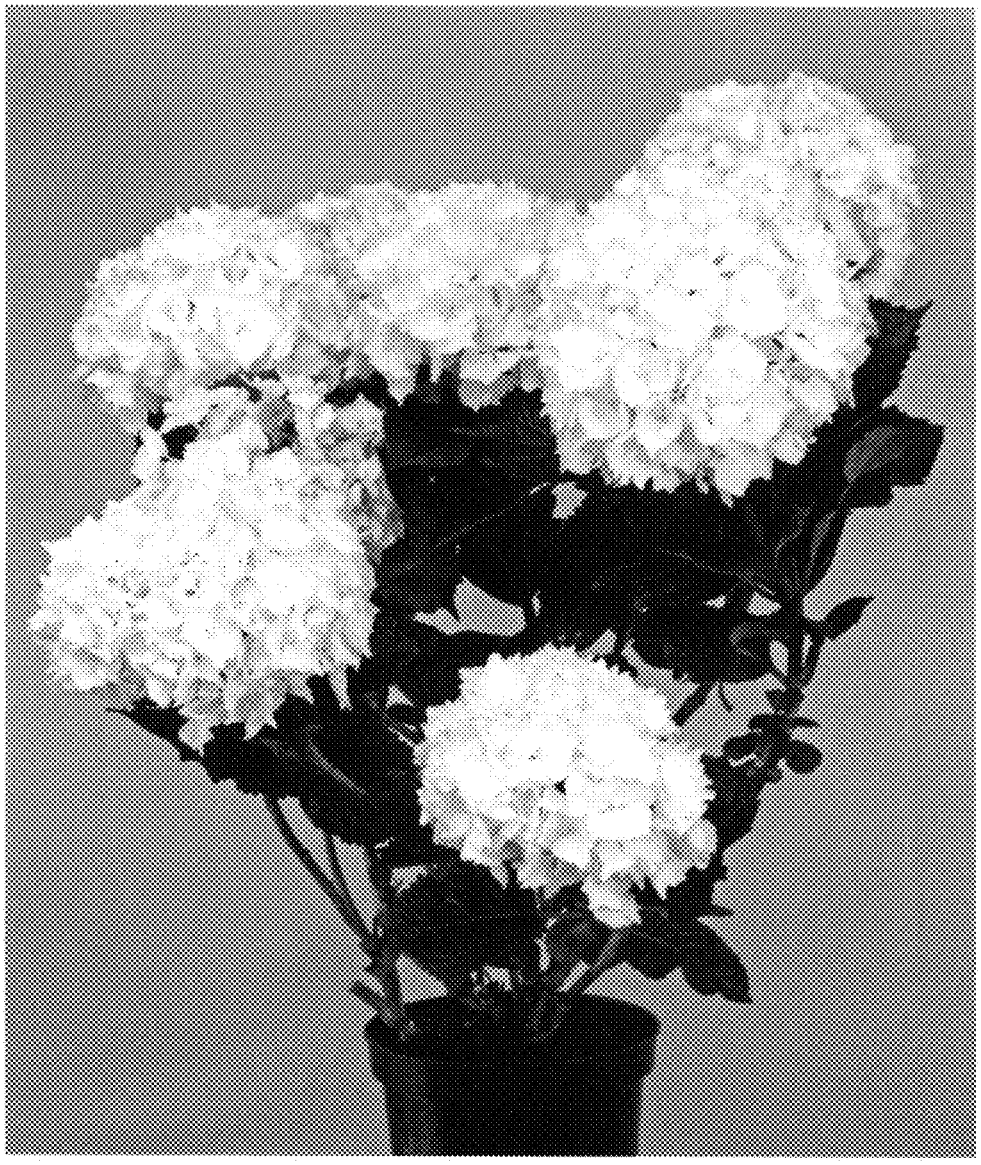

The photograph in FIG. 1 provides a side view of 'HORTMACLEPA' in bloom.

Figure 2:
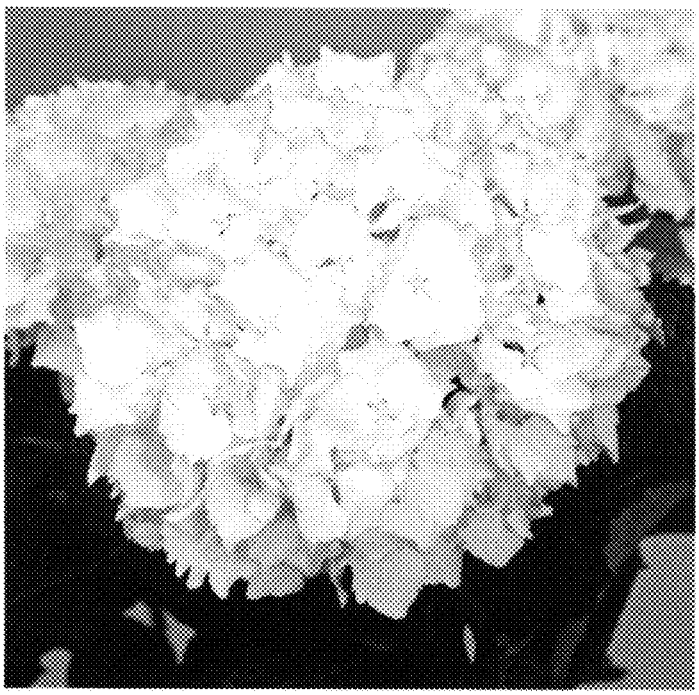

The photograph in FIG. 2 provides a close-up view of an inflorescence of 'HORTMACLEPA'.

Figure 3:
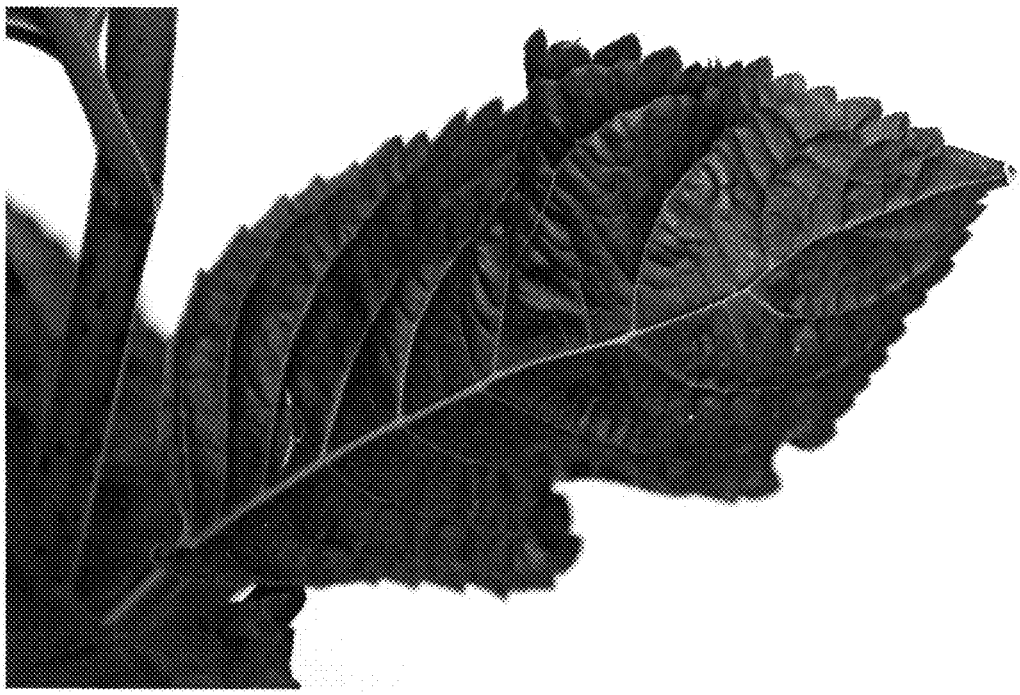

The photograph in FIG. 3 provides a close-up view of a leaf of 'HORTMACLEPA'.

The colors in the photographs are as close as possible with the photographic and printing technology utilized and the color values cited in the Detailed Botanical Description accurately describe the colors of the new *Hydrangea*.

DETAILED BOTANICAL DESCRIPTION

The following is a detailed description of three year-old plants of 'HORTMACLEPA' as grown in a greenhouse in 3-liter containers in Boskoop, The Netherlands. Phenotypic differences may be observed with variations in environmental, climatic, and cultural conditions. The color determination is in accordance with the 2007 R.H.S. Colour Chart of the Royal Horticultural Society, London, England, except where general color terms of ordinary dictionary significance are used.

General description:

*Blooming period.*—From May to August in a greenhouse in Boskoop, the Netherlands.

*Plant type.*—Deciduous shrub, mophead type *Hydrangea.*

*Plant habit.*—Broadly upright.

*Height and spread.*—An average of 1 m in height and 60 cm in spread.

*Hardiness.*—At least U.S.D.A. Zones 5 to 9.

*Diseases resistance.*—No susceptibility and resistance has been observed.

*Root description.*—Fine and fibrous.

*Propagation.*—Stem cuttings.

*Root development.*—An average of 6 months to finish a young plant from a cutting.

*Growth rate.*—Moderate.

Stem description:

*Stem shape.*—Rounded.

*Stem strength.*—Strong.

*Stem color.*—New growth; 144A, mature growth; between N199C and 200D.

*Stem size.*—An average of 39.4 cm in length and 8 mm in diameter.

*Stem surface.*—Glabrous, moderately lenticellate, lenticels; 7 per $cm^2$, an average of 2 mm in length and 1 mm in width, 187A in color.

*Stem aspect.*—Held at an average angle of 55° to horizontal.

*Internode length.*—An average of 5.3 cm.

*Branching.*—Low to moderately freely branching with an average of 10 lateral branches.

Foliage description:

*Leaf shape.*—Ovate to broadly ovate.

*Leaf arrangement.*—Opposite.

*Leaf division.*—Simple.

*Leaf base.*—Obtuse to short attenuate.

*Leaf apex.*—Apiculate.

*Leaf margins.*—Serrate.

*Leaf venation.*—Pinnate, color; upper side 144B, lower side 145A to 145B.

*Leaf size.*—An average of 11.8 cm in length and 8.9 cm in width.

*Leaf attachment.*—Petiolate.

*Leaf surface.*—Both surfaces; glabrous and moderately rugose, small tufts of very short hairs are present in the vein axils between the main vein and secondary vein on leaf undersides, average of 0.3 mm in length and 157A in color.

*Leaf color.*—Young upper surface; 137A, young lower surface; 146A, mature upper surface; between N137A and N189A, mature lower surface; 147B.

*Petioles.*—An average of 2.6 cm in length and 3.5 mm in diameter, color; upper surface 144B and lower surface 144A to 144B, both surfaces are glabrous and glossy.

Inflorescence description:

*Inflorescence type.*—Terminal panicle, flattened mophead in form comprised of a center region of fertile flowers surrounded by numerous single sterile florets.

*Lastingness of inflorescence.*—Sterile flowers; persistent for an average of 6 weeks, fertile flowers; an average of 5 days, flowers dry at maturity, self-cleaning.

*Inflorescence number.*—One per lateral stem.

*Inflorescence size.*—An average of 13.3 cm in height and 17.2 cm in diameter.

*Flower number.*—An average of 250 sterile florets and 75 fertile florets per panicle.

*Flower fragrance.*—None.

*Flower aspect.*—Sterile flowers; Upright to outward, fertile flowers; upright.

*Flower size.*—Sterile flowers; an average of 5.2 cm in diameter and 1.2 cm in depth, fertile flowers; an average of 6 mm in diameter and 4 mm in depth.

*Flower type.*—Rotate.

*Flower buds.*—Sterile flowers; an average of 1 cm in length and 8 mm in diameter, ovate in shape, color; NN155D, margins and base 61C to 61D, fertile flowers; an average of 4 mm in length and 3.5 mm in diameter, broad obovate to near globular in shape, color; ranging between 149C to 149D and 157B, base 144B.

*Pedicels.*—Sterile flowers; held at an average angle of 40°, an average of 2.3 cm in length and 1.5 mm in diameter, strong strength, color; 155C, matte surface sparsely covered with short soft hairs an average of 0.1 mm in length and NN155D in color, fertile flowers; held at an average angle of 20° from vertical (0° =vertical), an average of 4 mm in length and 1 mm in diameter, moderate strength, color; 145B to 145C, matte and glabrous surface and 150D in color.

*Petals.*—Sterile flowers; an average of 4, rotate arrangement, acute apex, cuneate base, entire margins, ovate and concave in shape, an average of 2.5 mm in length and 1.5 mm in width, upper surface; glabrous and matte, lower surface; glabrous and very slightly glossy, color; upper surface when opening; NN155D, upper half 145D, tips 59D, lower surface when opening; NN155D, tips slightly 59D, upper and lower surfaces when fully opened; petals of sterile flowers are dropped at maturity, color not fading, fertile flowers; an average of 4, occasionally 5, rotate in arrangement, ovate and slightly concave in shape, entire margin, acute apex, cuneate base, an average of 2 mm in length and 1.25 mm in width, upper and lower surface glabrous and matte, color; upper and lower surface when opening; NN155D, upper and lower surface when fully open; petals dropped at maturity, color not fading.

*Sepals.*—Sterile flowers; an average of 4, occasionally 5, rotate arrangement, broad deltoid to near reniform in shape, an average of 2.8 cm in length and 3.1 cm in width, bluntly acute apex, margin entire to coarsely crenate (average of 1 to 2 teeth per side) and ruffled, truncate to attenuate base, upper surface slightly rugose, glabrous, and matte, lower surface glabrous and matte, strong substance, color; when opening upper and lower surfaces; NN155D, margins 61D, when fully opened upper and lower surfaces; NN155D, margins 61C, color fading (antique/autumn phase) upper surface; 155B suffused with 144A and 144B, margins 61D, color fading (antique/autumn phase) lower surface; 155B suffused with 144A to 144B, margins 61C to 61D, fertile flowers; an average of 5, occasionally 6, rotate in arrangement, ovate in shape, entire margin, acute apex, broadly cuneate base, an average of 1.5 mm in length and 1 mm in width, both surfaces are glabrous and matte, color; upper and lower surface when opening and when fully opened; 145B to 145C, color not fading.

Reproductive organs: (present on fertile flowers and occasionally on sterile flowers).

*Stamens.*—Sterile flowers; an average of 8, anther; broad kidney-shaped, an average of 0.5 mm in length, and 155A in color, filament; an average of 1 mm in length and 144B to 144C in color, pollen is low in quantity and 155A in color, fertile flowers; an average of 8, anther; broad kidney-shaped, an average of 0.5 mm in length and 151A in color, filament; an average of 2 mm 150D in color, pollen is low and 155A in color.

*Pistils.*—Sterile flowers; an average of 3 pistils, an average of 1 mm in length, stigma; club-shaped and 150D in color, style is an average of 0.5 mm in length and 150D in color, ovary is 144B in color, fertile flowers; an average of 3, an average of 1 mm in length, stigma; club-shaped and 150D in color, style; an average of 0.5 mm in length and 150D in color, ovary is 144B in color.

*Fruit and seed.*—None observed to date.

It is claimed:

1. A new and distinct cultivar of *Hydrangea* plant named 'HORTMACLEPA' as herein illustrated and described.

* * * * *